United States Patent [19]

Laugal et al.

[11] Patent Number: 4,824,768
[45] Date of Patent: Apr. 25, 1989

[54] METHOD FOR FORMING PATTERNED ALUMINA FILM ELEMENT

[75] Inventors: Ruth C. O. Laugal, Union Lake; Adolph L. Micheli, Mt. Clemens, both of Mich.

[73] Assignee: General Motors Corporation, Detroit, Mich.

[21] Appl. No.: 127,985

[22] Filed: Dec. 3, 1987

[51] Int. Cl.$^4$ .............................................. G03C 5/00
[52] U.S. Cl. .................................. 430/323; 430/299; 430/317; 430/327; 430/330; 156/659.1
[58] Field of Search ............... 430/299, 313, 317, 323, 430/327, 329, 330; 156/659.1

[56] References Cited

U.S. PATENT DOCUMENTS

| | | | |
|---|---|---|---|
| 4,040,083 | 8/1977 | Saiki et al. | 357/54 |
| 4,613,404 | 9/1986 | Tabei | 156/643 |
| 4,634,495 | 1/1987 | Gobrecht et al. | 156/643 |

OTHER PUBLICATIONS

Vest, "Metallo-Organic Materials for Improved Thick Film Reliability", Final Report for Contract No. N00163-79-C-0352 for Naval Avionic Center (1980), Report Documentation page and pp. 86, 93, 118, 119 and Thermogram Nos. 46a, 46b, 46c and 47.
Vest, "Metallo-Organic Materials for Improved Thick Film Reliability", Final Report for Contract No. N00163-80-C-0449 for Naval Avionics Center (1982), Report Documentation page and pp. 28-30 and 64-66 and Appendix A2.

Primary Examiner—José G. Dees
Attorney, Agent, or Firm—Douglas D. Fekete

[57] ABSTRACT

A method is disclosed for forming an alumina film on a selected region of a surface without forming the film on an adjacent region. An ink film composed of aluminum caboxylate compound is applied to the surface and heated to partially decompose the compound. A positive photoresist layer is preferably applied to the partially decomposed layer and selectively irradiated to define a mask overlying the selected region. Unwanted photoresist material is dissolved from the adjacent region using an aqueous alkaline solution. It is found that the solution concurrently dissolves the underlying partially decomposed aluminum compound, without dissolving the compound protected by the mask. Thereafter, the mask is stripped, and the underlying aluminum compound is heated and further decomposed to produce the desired alumina film.

3 Claims, 1 Drawing Sheet

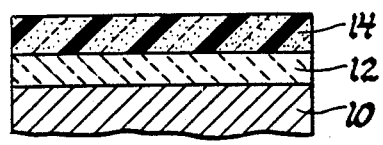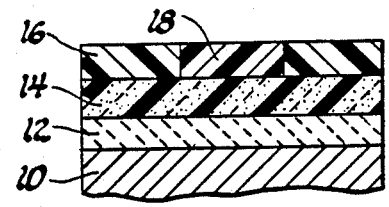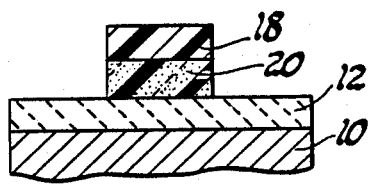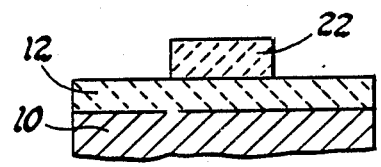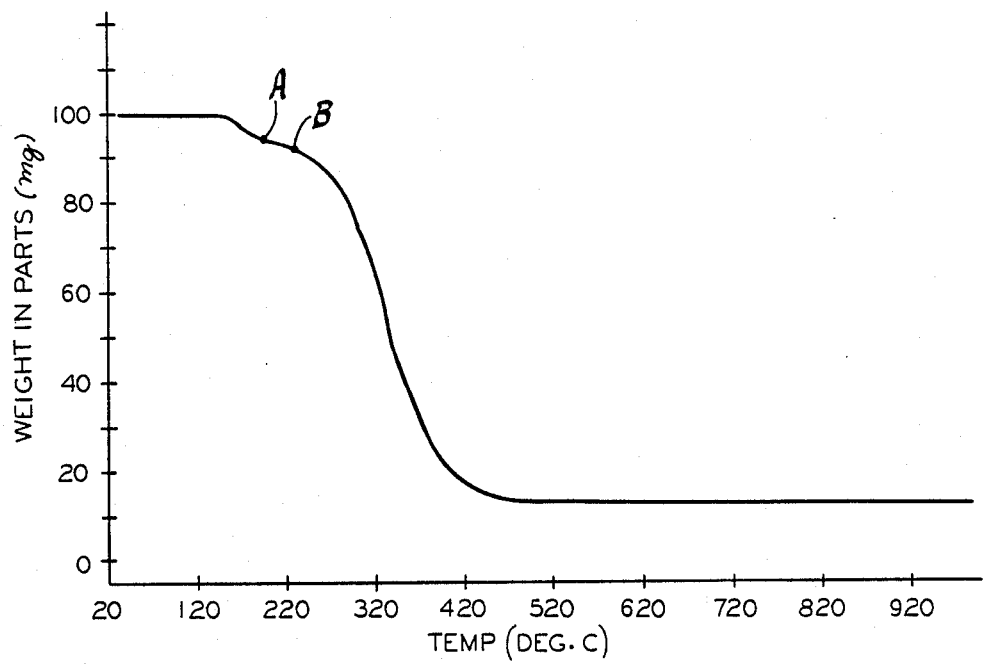

METHOD FOR FORMING PATTERNED ALUMINA FILM ELEMENT

BACKGROUND OF THE INVENTION

This invention relates to forming an aluminum oxide film element on a selected surface region by thermally decomposing an aluminum carboxylate compound. More particularly, this invention relates to such method that employs a photoresist mask to define the element and further comprises a pre-mask partial decomposition treatment of the aluminum compound to allow removal of unwanted aluminum compound in the same step and with the same solvent as nonmasking photoresist material, without disturbing the masked aluminum compound, to permit film definition without a separate etching operation.

In integrated circuit technology, elements composed of aluminum oxide, also referred to as alumina, are employed, for example, as gate insulators for ion selective field effect transistors (ISFET). Such elements are conventionally formed by sputtering a thin alumina film onto a substrate and etching the film to define the element. In etching the alumina film, a photoresist mask is employed to protect the film in the region of the element. A typical mask is formed by applying a photoresist layer and selectively exposing the photoresist layer to light in regions other than the element. The photoresist material is insoluble in aqueous alkaline solution as applied, but becomes soluble upon exposure to light. Thus, following irradiation, nonmask photoresist is washed from the surface using alkaline solvent, leaving the mask. Alumina is relatively insoluble in aqueous alkaline solution and thus is removed from unwanted regions in a separate etching operation. After etching, the mask is removed to expose the element.

It has been proposed to produce an alumina film by metallo-organic deposition (MOD), wherein an ink comprising an organic aluminum compound is applied and fired to form the alumina film. Because the organic aluminum ink is readily soluble in aqueous alkaline solution, when a photoresist mask is applied to unfired ink, the alkaline solvent used to remove the nonmask photoresist also washes the ink from the surface, including from under the mask. Thus, it has heretofore been necessary to fire the ink to form the alumina prior to applying the photoresist mask, in which case the alumina is etched in a separate step after the mask is formed.

It has now been found that a partial decomposition treatment of the organic aluminum compound prior to masking reduces the rate at which the aluminum material is dissolved by alkaline solution so as to suitably inhibit washing away of masked material, while still allowing removal of nonmasked material.

It is an object of this invention to provide an improved MOD process for producing an alumina film element by thermal decomposition of an organic aluminum compound, which process comprises a partial decomposition of the aluminum compound prior to applying and developing a photoresist layer, and which further comprises removal of unwanted aluminum compound by dissolution in alkaline solvent of the type used to remove nonmask photoresist. Masked regions of the partially decomposed aluminum compound remain substantially intact despite the solvent. In a preferred aspect of this invention, the unwanted aluminum compound is removed in the same step as the nonmask photoresist, thereby eliminating a separate etching step that would otherwise be required to pattern the film.

SUMMARY OF THE INVENTION

In accordance with this invention, an

In the accordance with this invention, an improved MOD method forms an alumina film on a predetermined region of a surface without forming the film on an adjacent region, permitting an element of the alumina film to be formed readily in a desired pattern. In a preferred embodiment, the MOD method comprises applying an ink formed of a thermally decomposable aluminum carboxylate compound uniformly onto both the pattern region and the adjacent region. The aluminum-containing ink is heated in air for a time and at a temperature sufficient to partially decompose the compound to produce an intermediate compound having reduced solubility in aqueous alkaline solution of the type used as solvent to remove nonmask photoresist material. The time and temperature of the partial decomposition treatment is dependent upon the particular aluminum carboxylate. In a preferred embodiment, ink composed of aluminum isopropoxideneodecanoate compound is partially decomposed at a temperature between about 200° C. and 225° C. for a time between about 45 and 60 minutes.

To pattern the partially decomposed film, the film is coated with a photoresist material and selectively exposed to light to produce a mask overlying the region of the intended element that is insoluble in aqueous alkaline solution. The photoresist layer is then contacted with aqueous alkaline solvent to dissolve the photoresist material from nonmask regions. Concurrently, the solvent also dissolves the underlying partially decomposed aluminum compound. In contrast, the mask is not dissolved and protects the underlying aluminum compound from dissolution. Furthermore, the solvent does not laterally wash away the aluminum compound underlying the mask, as would occur in the absence of the partial decomposition treatment. In this manner, aluminum compound remains in the pattern region, but is removed from the adjacent region.

After the unwanted aluminum compound is removed, the photoresist mask is removed using a suitable nonaqueous solvent to expose the underlying partially decomposed aluminum compound. The aluminum compound is then heated in air at a time and for a temperature sufficient to complete decomposition and form an alumina film element.

Thus, the method of this invention forms a thin alumina film only on a predetermined region of a surface, in contrast to a method that would form the film on an entire surface and thereafter etch to remove alumina from unwanted regions. The unwanted aluminum compound is removed in the same step and using the same solvent as nonmasking photoresist material. However, masked aluminum compound is not significantly disturbed. Thus, the method of this invention avoids an expensive and time-consuming etching operation and reduces the number of steps required to form a patterned alumina element, thereby reducing the time and expense required to manufacture an integrated circuit device in which element is employed.

DESCRIPTION OF THE DRAWINGS

The present invention will be further illustrated with reference to the drawings wherein:

FIGS. 1 through 4 schematically depict a sequence of steps for manufacturing an alumina film element in accordance with this invention; and FIG. 5 is a thermogravimetric analysis graph wherein the abscissa indicates temperature and the ordinate indicates weight.

DETAILED DESCRIPTION OF THE INVENTION

EXAMPLE

In a preferred example, described with reference to FIGS. 1 through 4, an alumina thin film was formed by thermal decomposition of aluminum isopropoxideneodecanoate compound.

Referring to FIG. 1, a preferred silicon wafer substrate 10 comprises a thermally grown silicon dioxide surface layer 12. An ink was prepared by dissolving one gram aluminum isopropoxideneodecanoate into one milliliter ultrapure grade xylene. The aluminum isopropoxideneodecanoate was formed by reacting aluminum isopropoxide with neodecanoic acid. The ink solution was applied onto layer 12 and uniformly distributed by spinning substrate 10 at about 4,000 RPM for about 120 seconds. The xylene vehicle was allowed to evaporate at ambient temperature, whereupon the ink residue formed a tacky film on the order of 5,000 Å thick. In accordance with this invention, the ink film was heated while exposed to air at about 225° C. for about 45 minutes to produce a partially decomposed film 14 in FIG. 1.

A positive working photoresist material was applied to film 14 and irradiated to produce a layer comprising an alkaline-soluble nonmask portion 16 and alkaline-insoluble mask 18, shown in FIG. 2. A preferred commercial photoresist material was obtained from Shipley Co., Inc., under the trade designation AZ-1350J and comprises an ortho-diazoketone compound dissolved in a vaporizable organic solvent. The commercial liquid was applied to layer 14 and distributed by spinning substrate 10 at about 5,000 RPM. Following drying, the photoresist material was prebaked at about 85° C. for about 10 minutes. Nonmask portions 16 of the photoresist layer were selectively exposed to ultraviolet light to convert the photoresist material to a carboxylic acid form soluble in aqueous alkaline solution, without exposing mask 18, so that mask 18 remained in alkaline-insoluble form.

Substrate 10 bearing the irradiated photoresist layer was immersed for about 30 seconds in 0.6 Normal aqueous alkaline solvent obtained from Shipley Co., Inc., under the trade designation Microposit Developer (used undiluted). The alkaline solution dissolved nonmask photoresist 16, but did not dissolve mask 18. In accordance with this invention, the alkaline solution concurrently dissolved the aluminum compound 14 underlying nonmask photoresist 16. However, the solvent did not significantly erode the partially decomposed aluminum compound 20 underlying mask 18, as shown in FIG. 3.

Mask 18 was removed by immersion in acetone for about five minutes, thereby exposing film 20. The surface bearing film 20 was heated in air at a temperature of about 800° C. for about one hour to complete decomposition of the aluminum compound and produce an alumina thin film element 22 shown in FIG. 4. The product thin film element 22 is between about 1,000 and 2,000 Å thick and suitable for use as an electrical insulator.

Comparative Example A

For comparison, the method of the Example was followed, but without the prepatterning partial decomposition treatment as in the present invention. The aluminum isopropoxideneodecanoate ink was applied in xylene solution and dried. A positive working photoresist layer was applied and irradiated to form a mask, as in the Example. When, however, the substrate bearing the photoresist layer was immersed in alkaline solvent as in the Example, the solvent dissolved the ink from the entire surface, including from underneath the mask. The resulting surface was substantially free of aluminum compound so that no oxide film element could be formed.

Comparative Example B

For comparison, the method of the Example was followed, but the aluminum organic compound was fully decomposed prior to applying the photoresist layer. The aluminum isopropoxideneodecanoate was applied in xylene solution, dried and fired in air at about 800° C. for one hour, thereby producing an alumina thin film covering the entire substrate surface. A photoresist layer was applied and irradiated as in the Example. The irradiated photoresist layer was immersed in the alkaline solvent used in the Example. Nonmasking photoresist material was dissolved by the solvent, but the alumina film was not significantly removed. Thus, additional steps were required to etch the alumina thin film from the unmasked substrate surfaces and thereby define the desired element.

Therefore, the MOD method of this invention forms an alumina film on a selected region of a surface, without forming the film on adjacent regions, by thermal decomposition of an aluminum carboxylate compound. Suitable aluminum compounds comprise an aluminum bonded to an oxygen of a carboxyl group of an organic ligand, as opposed to an organoaluminum compound having an aluminum-carbon bond. For charge balance, the aluminum in the preferred compound is bonded to three carboxyl ligands.

Upon heating, aluminum carboxylate compounds ultimately decompose to produce vaporizable organic byproducts and alumina, $Al_2O_3$. Although decomposition is preferably carried out in air, it is believed, because of the relatively low temperature, that decomposition does not involve reaction with ambient oxygen. Aluminum carboxylates generally have high solubility in alkaline solution, particularly alkaline solution of the type used to strip nonmasking positive photoresist material, so that the compound is washed away even though underneath a mask, as shown in Comparative Example A. In contrast, alumina derived from the aluminum organic compound is substantially insoluble in alkaline solution, as shown in Comparative Example B, so that an etch step is necessary to pattern the alumina film once formed.

In accordance with this invention, the aluminum carboxylate is subjected to a prepatterning partial decomposition treatment to reduce solubility by an amount that allows dissolution of the unmasked film in photoresist developer solvent, while inhibiting dissolution of masked compound. The time and temperature of the prepatterning treatment depends upon the particular ink compound. For an aluminum isopropoxideneodecanoate compound in the described embodiment, a preferred treatment comprises 45 to 60 minutes at 200° C. to 225° C. It is found that heating at a temperature less than about 200° C. does not satisfactorily inhibit dissolution of masked film, as evidenced by excessive undercutting of the mask. It is also found that treatment temperatures greater than about 225° C. significantly retard dissolution, undesirably extending the time required to remove the unwanted aluminum compound using photoresist solvent.

Decomposition of the aluminum isopropoxideneodecanoate compound in the Example is indicated by the thermogravimetric analysis in FIG. 5. Data was obtained using a Thermogravimetric Analyzer obtained from DuPont Corporation under the trade designation Model 9900. A solvent-free sample of the commercial compound was heated from room temperature at a rate of 10° C. per minute in air while continuously weighing the sample. FIG. 5 shows measured sample weight as a function of temperature. Weight loss at temperatures less than about 153° C. is mainly attributed to volatilization of the aluminum isopropoxideneodecanoate compound. At higher temperatures, decomposition of the aluminum isopropoxideneodecanoate compound produces organic byproducts that vaporize, resulting in weight loss. It is believed that decomposition proceeds in two stages. During a first stage occurring at temperatures less than about 287° C., the aluminum isopropoxideneodecanoate is believed to decompose to an intermediate aluminum compound, referred to as a partial oxide. At temperatures above 330° C., weight loss is attributed to further decomposition of the intermediate compound to produce the desired alumina. Above about 525° C., minimal further weight loss occurs, indicating a stable oxide. A preferred prepatterning temperature range is indicated between points A and B.

The decomposition temperature range depends upon the particular aluminum carboxylate compound, and also upon impurities in the ink, or additives such as metallo-organic or other compounds blended into the ink to affect film properties. In general, it is believed that a suitable prepatterning partial decomposition temperature is within a range sufficient to commence decomposition of the compound, but not sufficient to form product oxide; that is, sufficient to produce a reduced solubility intermediate but not decompose the intermediate.

In the Example, the partially decomposed film was patterned using a positive working photoresist wherein nonmask regions are irradiated to produce a soluble material. However, this invention may also be suitably carried out using a negative working photoresist material, wherein mask regions are irradiated. Nonmask negative photoresist is typically removed by nonaqueous solvent, so that an additional alkaline treatment may be necessary to remove the unwanted aluminum compound.

Also, although in the Example unwanted aluminum compound was dissolved using commercial photoresist developer solvent, other aqueous alkaline solution may be used, for example, potassium hydroxide.

While this invention has been described in terms of certain embodiments thereof, it is not intended that it be limited to the above description but rather only to the extent set forth in the claims that follow The embodiments of the invention in which an exclusive property or privilege is claimed are defined as follows:

1. A method for forming an alumina film on a selected region of a surface without forming the film on an adjacent region and such that the film is formed in a desired pattern, said method comprising applying uniformly onto both the selected region and the adjacent region an ink film comprising a thermally decomposable aluminum carboxylate compound, heating the ink film for a time and at a temperature sufficient to partially decompose the aluminum carboxylate compound to form a film having reduced solubility in aqueous alkaline solution, coating said partially decomposed film with a photoresist layer and selectively irradiating such that the selected region carries a photoresist mask insoluble in aqueous alkaline solution, removing the photoresist material from the adjacent region, thereby exposing the underlying partially decomposed aluminum compound, said partially decomposed compound being protected in the selected region by said mask, dissolving the exposed partially decomposed aluminum compound using aqueous alkaline solution, whereupon the photoresist mask protects the partially decomposed aluminum compound in the selected region from dissolution, removing the photoresist material from the selected region to expose the partially decomposed aluminum compound, and heating the partially decomposed aluminum compound for a time and at a temperature sufficient to further decompose the compound to produce an alumina film, whereupon the film is formed on the selected region but not on the adjacent region.

2. A method for forming an alumina film on a selected region of a surface without forming the film on an adjacent region and such that the film is formed in a desired pattern, said method comprising applying uniformly onto both the selected region and the adjacent region an ink film comprising a thermally decomposable aluminum carboxylate compound, heating the ink film in air for a time and at a temperature sufficient to partially decompose the aluminum compound to form a film having reduced solubility in aqueous alkaline solution, applying a photoresist layer that is essentially insoluble in aqueous alkaline solution onto the partially decomposed aluminum compound, selectively irradiating the photoresist layer overlying the adjacent region to produce a material that is soluble in aqueous alkaline solvent, whereupon the non-irradiated alkaline-insoluble photoresist material overlying the selected region forms a mask, exposing the surface bearing the irradiated photoresist layer to aqueous alkaline solvent to remove said soluble photoresist material from the adjacent region and to dissolve the underlying partially decomposed aluminum compound, whereupon the photoresist mask overlying the selected region protects the underlying compound from dissolution, removing the photoresist mask to expose the underlying aluminum compound, and heating the partially decomposed aluminum compound for a time and at a temperature sufficient to further decompose the compound to produce an alumina film, whereupon the film is formed on the selected region but not on the adjacent region.

3. A method according to claim 2 wherein the ink film is composed mainly of aluminum isopropoxideneodecanoate and is partially decomposed by heating at a temperature between 200° C. and 225° C. for a time between 45 and 60 minutes.

* * * * *